United States Patent [19]

Lynch, Jr. et al.

[11] 4,272,261

[45] Jun. 9, 1981

[54] AIR PURIFYING DEVICE

[76] Inventors: Patrick E. Lynch, Jr.; James M. Wimsatt, both of 155 Pintail Way, Carson City, Nev. 89701

[21] Appl. No.: 145,521

[22] Filed: May 1, 1980

[51] Int. Cl.³ .................... B01D 53/34; A61L 9/01
[52] U.S. Cl. .................................. 55/279; 55/276; 55/316; 55/413; 55/418; 55/472; 422/124
[58] Field of Search ............... 55/224, 225, 276, 279, 55/309, 316, 413, 414, 418, 472; 422/5, 123, 124

[56] References Cited

U.S. PATENT DOCUMENTS

| | | | |
|---|---|---|---|
| 1,098,506 | 6/1914 | Kelm | 55/418 |
| 1,614,817 | 1/1927 | Andrew | 422/124 |
| 2,415,621 | 2/1947 | Arnhym | 55/413 |
| 3,902,877 | 9/1975 | Swaim | 422/5 |

FOREIGN PATENT DOCUMENTS 494500  10/1938  United Kingdom ............ 55/309

OTHER PUBLICATIONS

"Ecologizer", The Good-Air Ca/90 Ecologizer, by Rush-Hampton Industries.

*Primary Examiner*—David L. Lacey
*Attorney, Agent, or Firm*—Townsend and Townsend

[57] ABSTRACT

The present invention provides an air purifying system which both filters and neutralizes odors in the air. A housing includes an inlet, an outlet, and an internal flow path from the inlet to the outlet. The outlet is preferably configured to provide a conical exhaust flow path. Fan means are located within the housing to move air through the housing along the flow path and out of the housing through the outlet. A filter is interposed in and spans the flow path of the housing to filter particulate matter from the air passing through the housing. An odor neutralizing chamber within the housing is partially interposed in the flow path. The chamber contains an odor neutralizing chemical which vaporizes in the presence of air. A mechanism is provided for controlling the amount of odor neutralizing chemical vapor which enters the air flowing through the housing.

8 Claims, 6 Drawing Figures

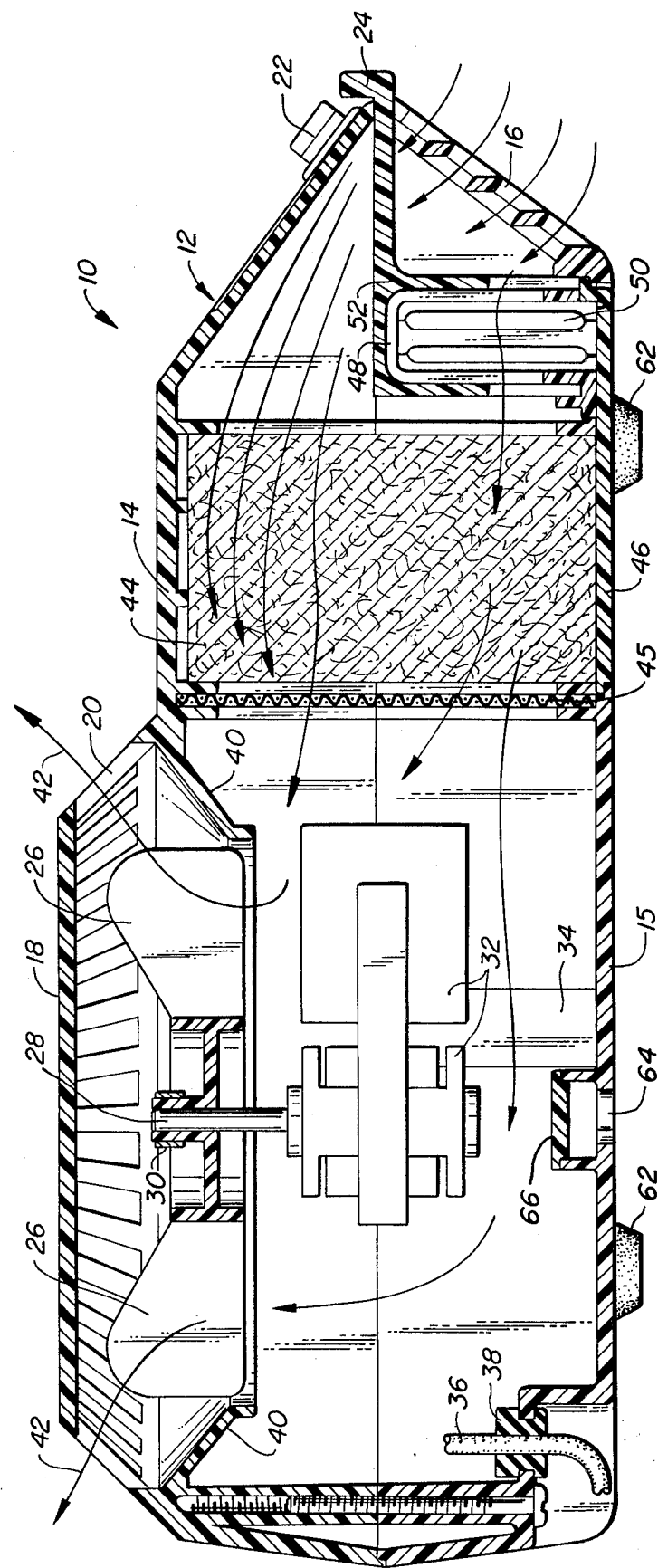

AIR PURIFYING DEVICE

BACKGROUND OF THE INVENTION

The present invention relates to air purifying devices, and in particular to such devices which both filter and neutralize odors in the air.

In hospitals and many other enclosed areas, it is desirable to provide an air purifying system which removes both particulate matter and odors which are molecular in nature. Many air circulation systems are in use in which filters are interposed in the flow path of an air stream to remove particulate matter, but filters are unable to remove molecular odors. Certain large filtration systems employ charcoal filters interposed in the flow path to remove molecular odors, but such systems are quite expensive, require frequent maintenance, and are impractical in many applications.

Various chemicals have been developed which neutralize molecular odors. Such chemicals are usually placed in fixed containers having small apertures so that air slowly moves through the containers by natural convection. Such chemicals have their own unpleasant odor, and cannot simply be interposed in a moving current of air provided by an active air circulation system because the odor caused by the chemical vapors would be overpowering.

A recent attempt has been made to incorporate an odor neutralizing chemical in an active air circulation system. This device is called the "Ecologizer" and is produced by Rush-Hampton Industries in Longwood, Florida. In this device, a crystal odor neutralizing chemical is located in the center of a duct through which air is forced by a fan. Most of the air propelled by the fan flows around the crystal so that only a relatively small amount of the crystal vaporizes and enters the air stream. Unfortunately, this device provides no filtration of particulate matter, and provides little control over the amount of odor neutralizing chemical vaporized so that either too much or too little of the odor neutralizing vapors are entrained in the air stream.

SUMMARY OF THE INVENTION

The present invention provides an air purifying system which both filters and neutralizes odors in the air. A housing includes an inlet, an outlet, and an internal flow path from the inlet to the outlet. Fan means are located within the housing to move air through the housing along the flow path and out of the housing through the outlet. A filter is interposed in and spans the flow path of the housing to filter particulate matter from the air passing through the housing. An odor neutralizing chamber within the housing is partially interposed in the flow path. The chamber contains an odor neutralizing chemical which vaporizes in the presence of air. A mechanism is provided for controlling the amount of odor neutralizing chemical vapor which enters the air flowing through the housing.

In the air purifying system of the present invention, the entire volume of air flowing through the housing is filtered to remove particulate matter. In addition, a controlled amount of air is exposed to the odor neutralizing chemical. This controlled amount of air mixes with the remainder of the air passing through the housing. The chemical neutralizes odors in substantially the entire volume of air passing through the housing, and is dispersed throughout the room by the exhausted air. The amount of odor neutralizing chemical which enters the airstream is controlled so that odors in the air are effectively neutralized without expelling excessive vapors into the room, which in itself can be a source of unacceptable odors.

The system of the present invention thus provides both complete air filtration and odor neutralization in a compact unit. Accordingly, all of the functions necessary for complete air purification are present in a single relatively simple and inexpensive device.

In the preferred embodiment of the present invention, the outlet in the housing is circular, and the housing includes a frustoconical ramp terminating in the outlet. As a result, the air flows out of the housing in a conical flow path at an approximately 45° angle from the axis of the fan. This flow path substantially prevents re-entry of the air into the housing through the outlet, increases the efficiency of the fan, and greatly increases the total volume of air which flows through the housing. Fan noise is also decreased, rending the device less obtrusive.

The novel features which are characteristic of the invention, as to organization and method of operation, together with further objects and advantages thereof will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 2 is a side sectional view of the preferred embodiment of FIG. 1;

DESCRIPTION OF THE PREFERRED EMBODIMENT

Figure 1:
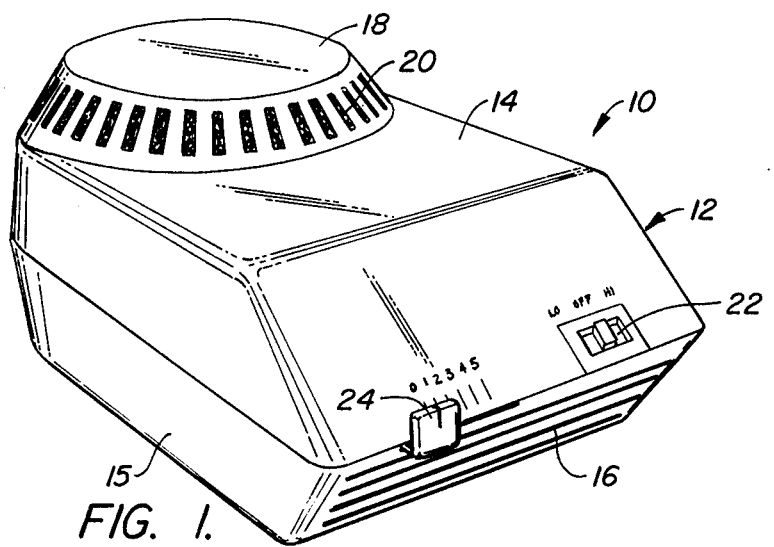
FIG. 1 is a perspective view of the preferred embodiment of the air purifying device of the present invention.

The preferred embodiment 10 of the air purifying device of the present invention is illustrated generally by way of reference to FIG. 1. Purifying device 10 includes a plastic shell 12 including an upper shell 14 and a lower shell 15. A grill 16 providing an air inlet is located in one end of lower shell 15. Upper shell 14 has a raised plateau 18 with a circumferential grill 20 which provides an air outlet. A switch 22 with positions for off, low and high is located at one end of housing 12 alongside a tab 24 providing a sliding adjustment with multiple positions.

The internal construction of air purifying device 10 is illustrated in detail by way of reference to FIG. 2. A fan 26 is located immediately beneath plateau 18. Fan 26 is attached to a drive shaft 28 by clip 30. Drive shaft 28 emanates from a conventional shaded pole motor 32 mounted on a pedestal 34 integrally molded with lower shell 15. Motor 32 is powered by a cord 36 passing through plug 38 for connection to an electrical outlet.

Fan 26 draws air into housing 12 through inlet 16, through the interior of the housing, and forces the air out through outlet 20. A frustoconical ramp 40 having an included angle of approximately 90° circumscribes fan 26 and terminates at outlet 20. As a result, fan 26 directs air outwardly in a conical fashion, as illustrated by arrows 42. Raised plateau 18 prevents the re-entry of air into housing 12 through outlet 20. As a result, fan 26 is extremely efficient in drawing air through the housing, far more efficient than a conventional axial outlet.

A filter element 44 is disposed within housing 12 upstream of fan 26. Filter element 44 employs a conventional filter material such as cotton polyester to remove particulate matter from the air as it flows through the housing. Filter element 44 spans the entire flow path area of the air passing through the housing so that all of the air passes through the element and is filtered thereby. A fixed screen 45 is located downstream of filter element 44. A removable plate 46 is located on the underside of housing 12 so that filter element 44 can be replaced or cleaned periodically when necessary.

A chamber 48 projects partially into the flow path of the air passing through housing 12. Chamber 48 contains a replaceable odor neutralizing element 50 which slowly vaporizes in the presence of air to neutralize molecular odors. Odor neutralizing element 50 can also be replaced by removing plate 46. A sliding gate 52 overlies odor neutralizing chamber 48, and is controlled by tab 24 on the exterior of the housing.

Figure 4:
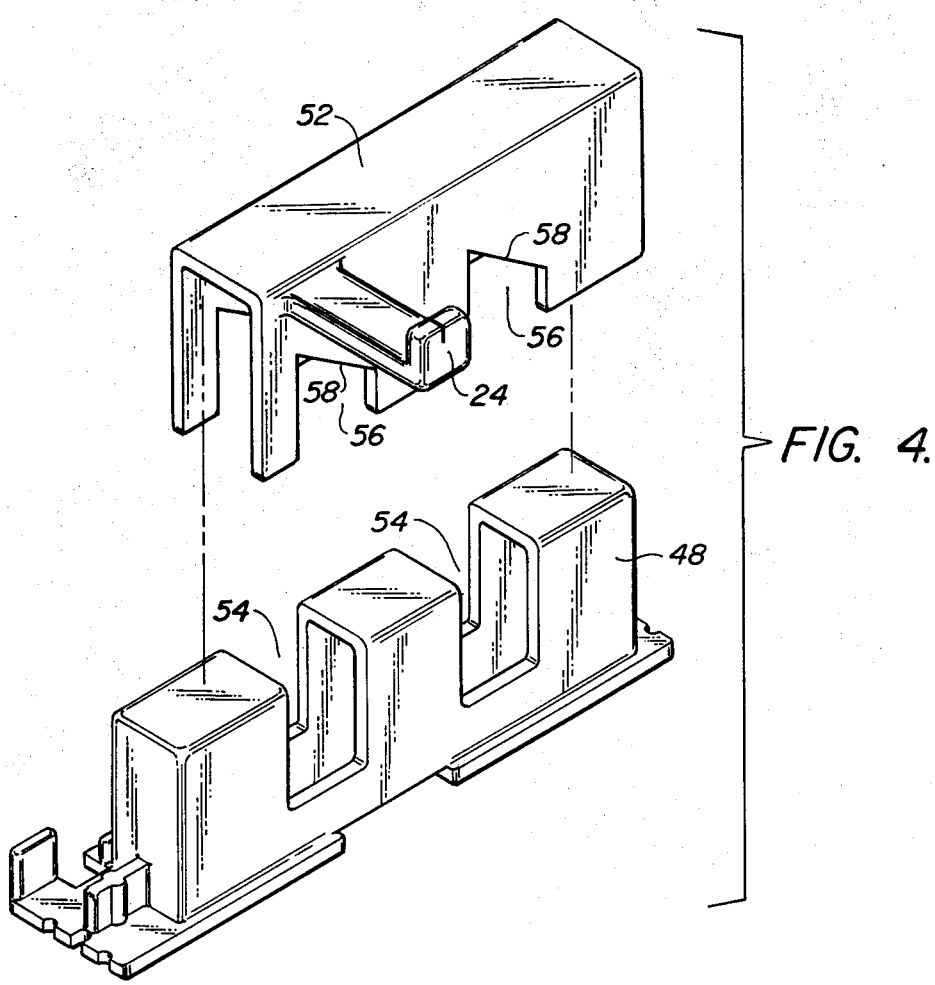
FIG. 4 is an exploded view of the sliding gate construction.

As illustrated in more detail by way of reference to FIG. 4, odor neutralizing chamber 48 has a pair of cut out portions 54. Sliding gate 52 has corresponding pairs of apertures 56 both front and back (not visible). Each aperture 56 in sliding gate 52 has the same width as cutout portions 54 in odor neutralizing chamber 48. Each aperture 56 has a ramp-shaped portion 58 at its upper extremity.

Figure 3A:
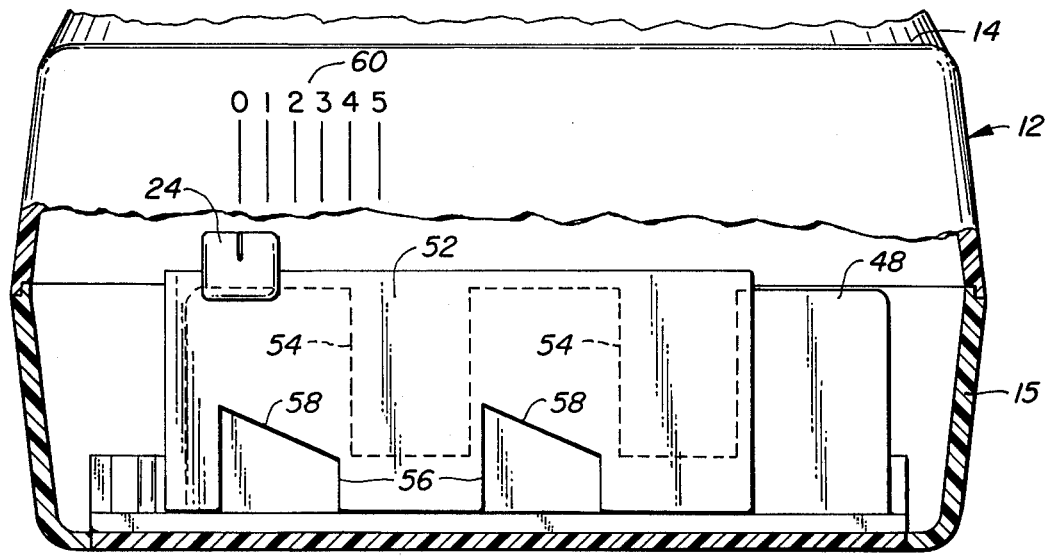
FIGS. 3A and 3B are front elevation, partially cut away views of the embodiment of FIG. 1 illustrating the movement of the sliding gate.

Referring to FIG. 3A, tab 24 controlling sliding gate 52 is at its extreme left or "closed" position, as illustrated by scale 60. In this configuration, apertures 56 in sliding gate 52 are out of alignment with cutout portions 54 in chamber 48. No air whatsoever is allowed to enter or leave odor neutralizing chamber 48, and odor neutralizing element 50 is isolated from the air passing through chamber 12.

Figure 3B:
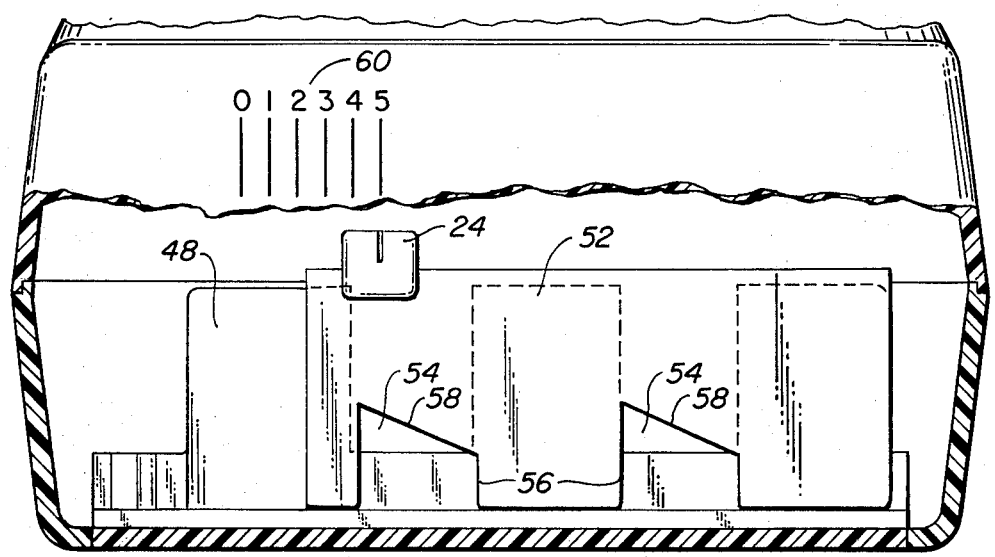

Referring next to FIG. 3B, tab 24 has been moved to the right to its fully open position, as illustrated by scale 60. In this position, apertures 56 in sliding gate 52 are directly aligned with cutout portions 54 in chamber 48. Although only the front apertures are illustrated in FIG. 3B, corresponding apertures are also present in the back portion of the sliding gate. Accordingly, vapor from odor neutralizing element 50 is allowed to enter the air passing through housing 12.

Figure 5:
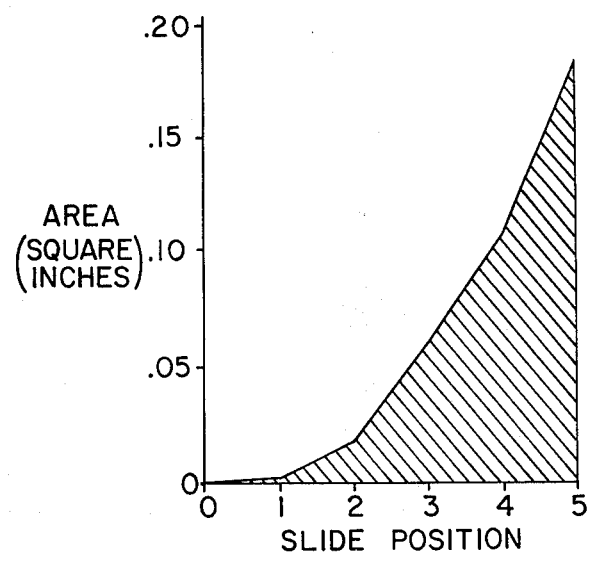
FIG. 5 is a graph of the opening provided by the sliding gate construction of the embodiment of FIG. 1.

Scale 60 indicates a plurality of intermediate positions for tab 24 between fully open and fully closed. The ramp-shaped upper extremities 58 of apertures 56 provide for a nonlinear increase in the area of overlap between the apertures and cutout portions 54 in chamber 48. It is readily apparent that scale 60 is linear. FIG. 5 is a graph of the area provided by the overlapping apertures and cutout portions, and indicates that movement of tab 24 results in an exponential increase in area. As a result, a wide variation in the amount of vapor released by odor neutralizing chamber 48 can be achieved by means of a simple linear adjustment.

In operation, fan 26 draws air into housing 12 through inlet 16. Unless tab 24 is in its fully closed position, the air passing through chamber 48 entrains odor neutralizing chemical vapors from element 50. When this air enters the main stream, it mixes with the remaining air to neutralize molecular odors in the entire air stream.

All of the air passing through housing 12 passes through filter element 44. Filter element 44 removes most particulate matter from the air stream. Since filter 44 is located downstream of odor neutralizing chamber 48, the vapors destroy odor causing bacteria in the filter element and the filter itself does not retain any odor. Both filter element 44 and odor neutralizing element 50 can be periodically replaced through access plate 46.

Air purifying device 10 can be mounted either horizontally or vertically. Pads 62 are located on the underside of shell 15 for mounting on a horizontal surface. A slot 64 in shell 15, blocked internally by cover 66 is used to mount device 10 on a wall or other vertical surface.

The air leaving filter 44 passes around shaded pole motor 32, and acts to cool the motor. This filtered and odor neutralized air is then directed outward from the chamber by fan 26 in a conical shape to enhance the efficiency of the air flow.

While a preferred embodiment has been illustrated in detail, it is apparent that modifications and adaptations of that embodiment will occur to those skilled in the art. However, it is to be expressly understood that such modifications and adaptations are within the spirit and scope of the present invention, as set forth in the following claims.

What is claimed is:

1. An air purifying system comprising:
   a housing including an air inlet, an air outlet, and an internal flow path from the inlet to the outlet;
   fan means within the housing adapted to move air through the housing along the flow path and out of the housing through the outlet;
   a filter interposed in and spanning the flow path in the housing to filter particulate matter from the air passing through the housing;
   an odor neutralizing chamber within the housing partially interposed in the flow path and in flow communication with the flow path and containing an odor neutralizing chemical which vaporizes in the presence of air; and
   means for controlling the amount of the odor neutralizing chemical vapor which exits the chamber and enters the air flowing through the housing.

2. The air purifying system of claim 1 wherein the odor neutralizing chamber is located upstream of the filter to neutralize odors in the air before it enters the filter so that the filter itself does not take on odors in the air.

3. The air purifying system of claim 1 wherein the fan means are located downstream of the filter.

4. The air purifying system of claim 1 wherein the controlling means comprises a sliding gate manually accessible from outside the housing and having a pair of openings selectively engaging a corresponding opening in the odor neutralizing chamber.

5. The air purifying system of claim 4, or 6 wherein the openings in the chamber and the openings in the sliding gate overlap to provide triangular passageways of related dimensions so that movement of the sliding gate results in a generally exponential increase in the size of the passageways.

6. The air purifying system of claim 1 or 6 wherein the air outlet is generally circular, and wherein the housing includes a frustoconical ramp opening into the outlet and having an included angle of approximately 90° so that the air is directed outwardly through the outlet in a conical flow path and air outside the housing is not drawn into the housing through the outlet.

7. An air purifying system comprising:
- a housing including an air inlet, a generally circular air outlet, a frustoconical ramp opening into the outlet and having an included angle of approximately 90°, and an internal flow path from the inlet to the outlet;
- fan means located within the housing proximate the frustoconical ramp and adapted to move air through the housing along the flow path and out of the housing through the outlet in a generally conical flow path;
- a filter interposed in and spanning the flow path in the housing to filter particulate matter from the air passing through the housing;
- an odor neutralizing chamber within the housing partially interposed in the flow path and in flow communication with the flow path and containing an odor neutralizing chemical which vaporizes in the presence of air; and
- means for controlling the amount of the odor neutralizing chemical vapor which exits the chamber and enters the air flowing through the housing.

8. An air purifying system comprising:
- a housing including an air inlet, an air outlet, and an internal flow path from the inlet to the outlet;
- fan means located within the housing near the air outlet to draw air into the housing through the inlet and along the flow path within the housing, and expel the air through the outlet;
- a filter interposed in and spanning the flow path within the housing to filter particulate matter from the air passing through the housing;
- an odor neutralizing chamber within the housing upstream of the filter, said odor neutralizing chamber being partially interposed in the flow path and in flow communication with the flow path and containing an odor neutralizing chemical which vaporizes in the presence of air, said odor neutralizing chamber including at least one pair of openings located in confronting walls in the chamber; and
- a sliding gate overlapping the odor neutralizing chamber and having a control member manually accessable from outside the housing, said sliding gate having at least one pair of openings selectively engaging the openings in the chamber to control the portion of air passing through the housing which flows through the odor neutralizing chamber and thereby control the amount of odor neutralizing chemical vapor which enters the air flowing through the housing.

* * * * *